United States Patent

Jonas

Patent Number: 5,463,056
Date of Patent: Oct. 31, 1995

[54] THIOPHENE DERIVATIVES

[75] Inventor: Friedrich Jonas, Aachen, Germany

[73] Assignee: Agfa-Gevaert AG, Leverkusen, Germany

[21] Appl. No.: 249,343

[22] Filed: May 27, 1994

[30] Foreign Application Priority Data

Jun. 8, 1993 [DE] Germany .......................... 43 19 042.1

[51] Int. Cl.[6] .................................................. C07D 495/04
[52] U.S. Cl. ............................ 544/350; 544/48; 544/105; 549/15; 549/50
[58] Field of Search ................................................ 544/350

[56] References Cited

U.S. PATENT DOCUMENTS

| | | | |
|---|---|---|---|
| 3,882,122 | 5/1975 | Hagen | 424/250 |
| 4,987,042 | 1/1991 | Jonas et al. | 429/213 |
| 5,111,327 | 5/1992 | Blohm et al. | 526/256 |

FOREIGN PATENT DOCUMENTS 4118704  12/1992  Germany .

OTHER PUBLICATIONS

*Heterocycles–An International Journal for Reviews and Communications in Heterocyclic Chemistry*, Founded by Tetsuji Kametani; The Japan Institute of Heterocyclic Chemistry, Elsevier Science Publishers vol. 34 No. 6, pp. 1191–1200., Chimirri et al. (1992).

*Synthetic Metals*, vol. 55 Nos. 2 & 3, Mar. 22, 1993 pp. 960–965; Pomerantz et al.

*Primary Examiner*—Philip I. Datlow
*Attorney, Agent, or Firm*—Connolly & Hutz

[57] ABSTRACT

Thiophene derivatives of formula (I)

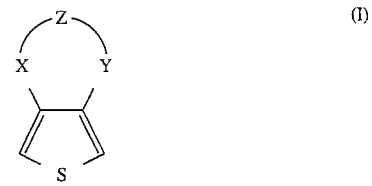

wherein

X and Y are the same or different O, S or N—$R^3$,

Z is a $C_1$–$C_6$-alkylene residue that may be substituted by $R^1$ and $R^2$, $R^1$, $R^2$ are the same or different hydrogen, or —$(CH_2)_n$—$OR^4$, —CH=$CH_2$ or

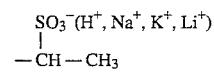

n is 1 to 10, $R^3$ is aryl, $C_{1-18}$-alkyl or H, $R^4$ is $SO_3^-(H^+,Na^+,K^+,Li^+)$ or —$(CH_2$—$CH_2$—$O)_m$—$R^5$, m is 1 to 10 and $R^5$ is alkyl with 1 to 6 C atoms, wherein compounds in which X and Y are both O and $R^1$ and $R^2$ are both hydrogen atoms are excluded, are suitable for the preparation of polythiophenes which can be used as organic electrical conductors.

2 Claims, No Drawings

THIOPHENE DERIVATIVES

Polythiophenes are well-known in the literature as organic conductors (U.S. Pat. No. 4,987,042).

Their properties, such as workability or long-term stability, are not yet adequate for all technical applications. There is therefore a requirement for polythiophenes with improved properties.

Polythiophenes are prepared by the chemical or electrochemical polymerisation of monomeric or oligomeric thiophenes.

In order to improve the properties of polythiophenes it is therefore necessary to synthesise new thiophene monomers or oligomers.

The present invention provides new thiophenes of formula (I), suitable for the preparation of electrically conducting polymers,

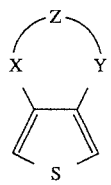
(I)

wherein

X and Y are the same or different O, S or N—$R^3$,

Z is a $C_1$–$C_6$-alkylene residue that may be substituted by $R^1$ and $R^2$, $R^1$, $R^2$ are the same or different hydrogen, or —$(CH_2)_n$—$OR^4$, —CH=$CH_2$ or

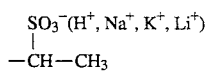

n is 1 to 10, $R^3$ is aryl, $C_{1-18}$-alkyl or H, $R^4$ is $SO_3^-$($H^+$,$Na^+$,$K^+$,$Li^+$) or —$(CH_2$—$CH_2$—$O)_m$—$R^5$, m is 1 to 10 and $R^5$ is alkyl with 1 to 6 C atoms, wherein compounds, in which X and Y are both O and $R^1$ and $R^2$ are both hydrogen, are excluded.

The preparation of the thiophenes of formula (I) according to the present invention takes place according to the following reaction path:

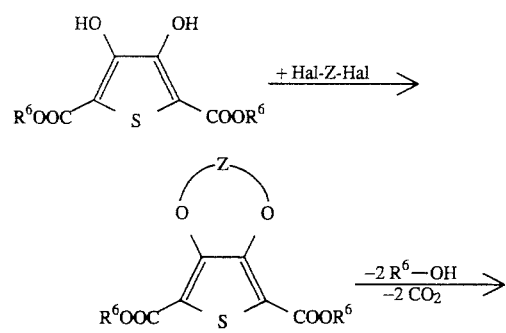

wherein the remaining symbols $R^6$ are alkyl residues with 1 to 6 C atoms,

Hal is a halogen atom from the series fluorine, chlorine, bromine or iodine, while Z has the meaning given above.

A further method for the preparation of the thiophenes of formula (I) according to the present invention is represented by the following reaction path:

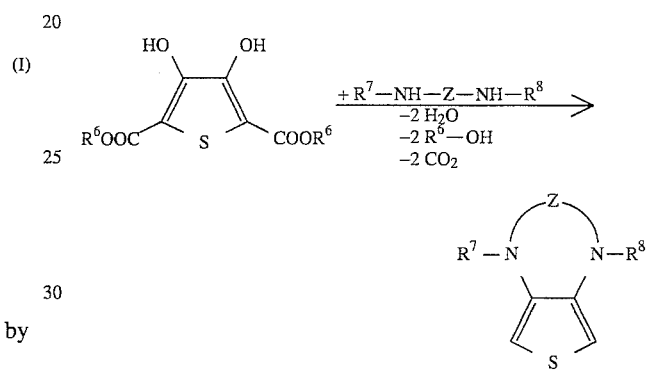

$R^7$ and $R^8$ are hydrogen, aryl, or $C_{1-18}$ alkyl,

Z has the meaning given above and is preferably an alkylene group with 1 to 6 C atoms that cannot be substituted further.

The two reaction paths represented should be understood as examples and do not exclude other preparation methods for the thiophenes of formula (I) according to the present invention.

The thiophenes of the formula are very suitable primary materials for the preparation of workable and electrically conducting polythiophenes.

The polymers are obtained by a well-known method through oxidising condensation with persulphates or iron (III) salts and are suitable for imparting antistatic properties to synthetic composites, for example, photographic films.

EXAMPLE

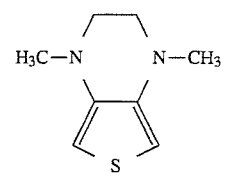

69.6 g of 3,4-dihydroxythiophene-2,5-dicarboxylic acid dimethyl ester, 28.2 g of N,N'-dimethyl-1,2-ethylenediamine, 0.5 g of p-toluenesulphonic acid, 100 ml of N,N-dimethylacetamide and 250 ml of toluene are stirred for 24 hours under reflux to a water trap. The reaction is then cooled to 20° C. and diluted with 100 ml of toluene. The solution is extracted four times, each time with 200 ml of 5% by weight of hydrochloric acid. The combined HCl phases are rendered alkaline with 10% by weight of NaOH and extracted three times, each time with 150 ml of toluene. The combined phases are fractionally distilled. Kp.=125°–130° C./0.9 mbar. Yield: 8.2 g.

I claim:

1. Thiophene derivatives of formula (I)

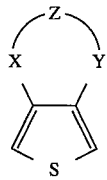 (I)

wherein

X and Y are N—$R^3$,

Z is a $C_2$-alkylene residue that may be substituted by $R^1$ and $R^2$, $R^1$ and $R^2$ are the same or different and are hydrogen, or —$(CH_2)_n$—$OR^4$, —CH=$CH_2$ or

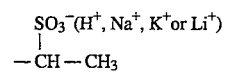

n is 1 to 10, $R^3$ is aryl, $C_{1-18}$-alkyl or H, $R^4$ is $SO_3^-$($H^+$,$Na^+$,$K^+$or $Li^+$) or —$(CH_2CH_2$—$O)_m$—$R^5$, m is 1 to 10 and $R^5$ is alkyl with 1 to 6 C atoms.

2. The thiophene derivative as claimed in claim 1, wherein said thiophene derivative is of the formula

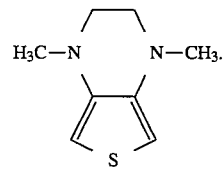

* * * * *